(12) United States Patent
Macoviak

(10) Patent No.: US 6,673,041 B1
(45) Date of Patent: *Jan. 6, 2004

(54) CATHETER SYSTEM FOR SURGICAL ACCESS AND CIRCULATORY SUPPORT OF THE HEART

(75) Inventor: John A. Macoviak, La Jolla, CA (US)

(73) Assignee: Cardeon Corporation, Cupertino, CA (US)

(*) Notice: Subject to any disclaimer, the term of this patent is extended or adjusted under 35 U.S.C. 154(b) by 322 days.

This patent is subject to a terminal disclaimer.

(21) Appl. No.: 09/652,231

(22) Filed: Aug. 29, 2000

Related U.S. Application Data

(63) Continuation of application No. 09/060,412, filed on Apr. 14, 1998, now Pat. No. 6,110,145, which is a continuation-in-part of application No. 08/632,883, filed on Apr. 16, 1996, now Pat. No. 5,738,649.

(51) Int. Cl.[7] .............................................. A61M 29/00
(52) U.S. Cl. ............................ 604/101.01; 604/101.03; 604/43
(58) Field of Search ....................... 604/101.01, 101.03, 604/101.05, 43; 606/194, 108

(56) References Cited

U.S. PATENT DOCUMENTS

| | | | | |
|---|---|---|---|---|
| 4,836,204 A | * | 6/1989 | Landymore et al. ... | 604/101.01 |
| 5,458,574 A | * | 10/1995 | Machold et al. ....... | 604/101.01 |
| 6,110,145 A | * | 8/2000 | Macoviak .............. | 606/101.01 |

* cited by examiner

Primary Examiner—Julian W. Woo
(74) Attorney, Agent, or Firm—Fulwider Patton Lee & Utecht, LLP

(57) ABSTRACT

Described is a closed chest intravascular catheter system for a simultaneous biventricular approach to (1) intravascular cardiopulmonary surgery; (2) acute or prolonged mechanical circulatory support. The catheter system includes a left heart catheter and a right heart catheter with flow control members that segment the circulatory system into subcirculations of cardiopulmonary support. The left heart catheter has an elongated shaft with a first flow control member positioned at the entry site into a peripheral artery, a second flow control member positioned in the proximal descending aorta, a third flow control member positioned in the ascending aorta, and a fourth flow control member positioned within the left ventricle. The right heart catheter has an elongated shaft with a first flow control member positioned at the entry site into a vein, a second flow control member positioned within the right atrium, a third flow control member positioned within the coronary sinus, and a fourth flow control member positioned through the pulmonic valve. Alternatively, in a transseptal approach, the left or right heart catheter can be advanced across the atrial septum of the heart. Each catheter has a main lumen for insertion of an imaging system and robotic instruments into the chambers of the heart. Each catheter includes a flexible distal section with a removable guide for directing the catheter through the chambers of the heart and, optionally, a proximal limb branch with a fifth flow control member for perfusing or draining the peripheral vessel at the entry site.

32 Claims, 8 Drawing Sheets

CATHETER SYSTEM FOR SURGICAL ACCESS AND CIRCULATORY SUPPORT OF THE HEART

CROSS REFERENCE TO RELATED APPLICATIONS

The present application is a continuation of application Ser. No. 09/060,412, filed Apr. 14, 1998, now U.S. Pat. No. 6,110,145, which is a continuation-in-part of application Ser. No. 08/632,883, filed Apr. 16, 1996 now U.S. Pat. No. 5,738,649.

FIELD OF THE INVENTION

This invention relates to a catheter system that facilitates cardiopulmonary surgeries and enables prolonged circulatory support of the heart.

BACKGROUND OF THE INVENTION

Heart surgery has generally required major open chest surgical procedures that put the patient at risk. Relatively high mortality rates and complications result from such invasive surgeries. Further, the surgeries require extensive hospitalization and recuperation time.

Surgical methods to correct heart problems are desirable which do not require open chest approaches. Some surgical techniques have been described for particular applications employing an intra-aortic catheter introduced into the vascular system of the patient. An example of such a technique may be found in U.S. Pat. No. 5,458,574. Endovascular techniques described to date, however, typically are not designed for all heart surgical procedures and do not provide access for robotic instruments to both sides of the heart.

Catheters have been described which access the left ventricle, for example, but there are none that are capable of surgically functioning on the right side of the heart. Further, such described catheters do not provide for a means to cross the atrial septum or provide for prolonged right or left ventricular bypass using an external pump, to mechanically support a reversibly failed heart in a closed chest procedure. Such a system which could be placed in both sides of the heart could more effectively resuscitate many cardiac arrest victims than other devices because ventricular decompression would be achievable.

Current methods further do not provide for selective cerebral perfusion, antegrade aortic flow, pulmonary artery flow or peripheral access vessel perfusion and drainage. Such mechanisms are necessary to minimize complications of a vast array related to proper direction of blood flow in the body.

Current methods do not take into account the desirability of perfusing the pulmonary artery or draining the left ventricle for prolonged support of the contracting but failed ventricle, via peripheral access for prolonged isolated right or left or simultaneous biventricular support. A system is needed which enables a broader range of endovascular cardiac surgical procedures, a method for prolonging heart support for certain surgical procedures and a method to mechanically support a reversibly failed heart to achieve direct circulatory arrest, with isolated cerebral perfusion using conventional heart and lung support machines.

SUMMARY OF THE INVENTION

The present invention provides a peripheral vascular catheter system versatile enough to access both sides of the heart, provide for prolonged heart support (to mechanically support a reversibly failed heart) to achieve deep hypothermic circulatory arrest with isolated or compartmentalized perfusion enabling surgery on the heart while controlling blood flow, including rate of flow, pressure, temperature, and the perfusion of selected chemicals, to selected parts of the body including but not limited to the brain, spinal cord, lungs, and heart. The invention can also be used to decompress selected chambers of the heart, which may allow some procedures to be performed without the need to stop the heart. The invention can further be used to perfuse a saline solution or the like to selected chambers of the heart to create a clear or bloodless operating field.

The subject biventricular vascular catheter system comprises (a) an elongated catheter shaft configured to be advanceable from a peripheral vessel or artery to and through all chambers of the heart, including across the ventricular or atrial septum, having a proximal end adapted to extend out of the patient and a distal end adapted to move through the patients arteries or vessels and the chambers of the heart, the distal end having multiple fenestrations and a first inner lumen extending therein from a port in the distal end of the shaft to a location in the proximal end; and (b) at least one and preferably a succession of flow control members positioned along the catheter shaft used to isolate or compartmentalize the blood flow to selected parts of the patient's body.

In one embodiment configured for entry through a femoral artery or vein, to the left or right heart respectively, the first flow control member is located at the proximal end of the catheter shaft proximate the site of entry of the shaft into the patient, the second flow control member is located distal to the first flow control member and is dimensioned and configured so that it sits in the proximal descending thoracic aorta, a third flow control member distal to the second flow control member is dimensioned and configured so that it seats between the coronary ostia and the brachiocephalic artery, and a fourth flow control member distal to the third flow control member is dimensioned and configured so that it seats in the left ventricular outflow tract. Useable flow control members include, but are not limited to, expandable or inflatable members such as an inflatable balloons and valves including collapsible/expandable valves of various configurations including retrograde valves, antegrade valves, and various central flow and peripheral flow valves. A combination of valves and inflatable members may be is used as appropriate for a given procedure, thus In some embodiments, the catheter body can include one or more antegrade and retrograde valves, as well as one or inflatable balloons.

Inflatable balloons and collapsible/deployable valves are well known in the industry and any desirable or practical such inflatable balloon or deployable valve may be used. Inflatable balloons typically include an interior chamber that is in fluid communication with an inflation lumen extending within the catheter shaft from a location from within the respective flow control member to a location in the proximal portion which is adapted to extend out of the patient.

Preferably, the catheter system will also include a second limb branch catheter connected to the catheter shaft at the proximal end, the limb catheter disposed to provide for drainage or perfusion of the peripheral vessel used as an entry for the catheter shaft in order to protect the limb vasculature. Such limb catheters allow drainage or perfusion of the vessel entered to permit continual placement of the catheter for several days, if necessary, for subacute cardiac assist. If neck vessels are accessed, for example, metabolic monitoring access to that limb or to cerebral circulation would be permitted.

In one preferred embodiment, the catheter system preferably includes a self-sealing dual diaphragm chamber instrument entry port branching from the more distal-ending channel of the catheter which has inflow and outflow ports to remove the air from the chamber to prevent an air embolus from occurring and to allow for the safe introduction of large devices.

In another preferred embodiment of the catheter system, the catheter has a catheter guide, preferably with at least one fenestration which enables the guidance of the catheter into and through the chambers of the heart and which may be removed from the catheter while the catheter is located within the heart.

A further preferred embodiment includes multiple circumferential rings which extend axially around the shaft along a portion of the distal end of the shaft, which rings facilitate the movement of the catheter through the heart. The rings are further supported by struts which connect the rings to one another. The struts are arranged so that they are positioned at varying points around the circumference of the catheter tip to prevent kinking.

The catheter system will further preferably accommodate the selective perfusion or drainage of blood either separately or at the same time from within chosen isolated portions of the patients arteries or vessels in which the catheter is deployed.

The system described here encompasses a number of benefits including the following:

(a) the ability to perform intravascular cardiac and pulmonary surgery through the less complicated peripheral access as compared to standard sternotomy or thoracotomy;

(b) the system lessens blood loss, infection risk, pain, hospital stays, expense and delays in return to full activity;

(c) there would be an expected decrease in the possibility of air emboli to the brain when performing surgery inside the heart and with the chest closed compared to current open heart techniques;

(d) better control of myocardial temperature is afforded compared to open chest approaches;

(e) the ability to isolate sub-circulation regions by selectively inflating the compartmentalizing flow control members to isolate sub-circulations such as the coronary, cerebral, pulmonary, neck and limb, and spinal or thoracic sub-circulations;

(f) the ability to perform antegrade aortic perfusion which avoids malperfusion;

(g) the ability to perform pulmonary artery perfusion which bypasses the right ventricle;

(h) the ability to optimally support the acutely failed heart by decompressing ventricles peripherally for acute and subacute mechanical circulatory support which would thus lead to an expected decrease in likelihood of infection, bleeding and pain compared to open chest cannulation for total ventricular support;

(i) the ability to create clear bloodless operating fields within the heart; and (j) the ability to selectively decompress selected chambers of the heart, which may allow the completion of some procedures without intentional cardiac arrest.

Some of the major goals of the catheter system disclosed here are to provide a catheter and multiple compartment flow control member system, placed by cutdown or percutaneous techniques, for peripheral vessel entry to accomplish intravascular cardiopulmonary biventricular or two-sided access to robotic surgery techniques of intra-cardiopulmonary structures, provided by a system of single and/or double (major) channel catheters; acute (for a period of minutes) deep hypothermic circulatory arrest with the option for selective cerebral perfusion to enable intra-cardiopulmonary surgery; subacute (over a period of days) cardiopulmonary mechanical support, with antegrade aortic and/or pulmonary artery perfusion, biventricular decompression and peripheral vessel protection, to allow recovery of reversible heart failure.

Definitions

"Acute circulatory arrest" refers to the event where the patient's body is cooled (usually to about 10° C.), the assisting blood pump is stopped, and the blood is drained from the body.

"Subacute mechanical support" refers to the event where the circulation is mechanically assisted for multiple days.

"Reversible heart failure" refers to an acutely injured heart which is expected to recover over time.

"Retrograde" and "antegrade" when used herein in relation to the patient's vasculature, relate to the direction of normal blood flow and to the direction opposite normal blood flow through a vessel, respectively.

The terms "proximal" and "distal" when used herein in relation to instruments used in a cardiac procedure, refer to directions closer and farther away, respectively, from that end of the instrument which is held or manipulated by the operator performing the procedure.

"Flow Control Valve" refers to any useable valve including, but not limited to, collapsible valves, which can be selectively expanded or inflated, of various configurations including various central flow and peripheral flow control valves. The valves may be retrograde or antegrade valves as appropriate. Moreover, the valves may be configured to occlude or inhibit fluid flow, hinder fluid flow, direct fluid flow, and occlude or hinder fluid flow in one direction while allowing fluid flow in another. Typically, the flow control valves are external to the catheter and are deployable to control the flow within the circulatory vessle in which they are placed. Antegrade flow control valves allow a greater flow in the antegrade direction than in the retrograde direction. Whereas, retrograde flow control valves allow a greater flow in the retrograde direction than in the antegrade direction.

Terms relating to anatomical parts have the meaning ascribed to them in the art and when they are coupled with an instrument part (e.g. supra-coronary inflation member) they indicate where in the body the instrument part is to be located.

Other terms used herein, unless otherwise defined herein, have the meanings commonly used by those of skill in the art of cardiac surgery.

DETAILED DESCRIPTION OF THE INVENTION

Figure 1:
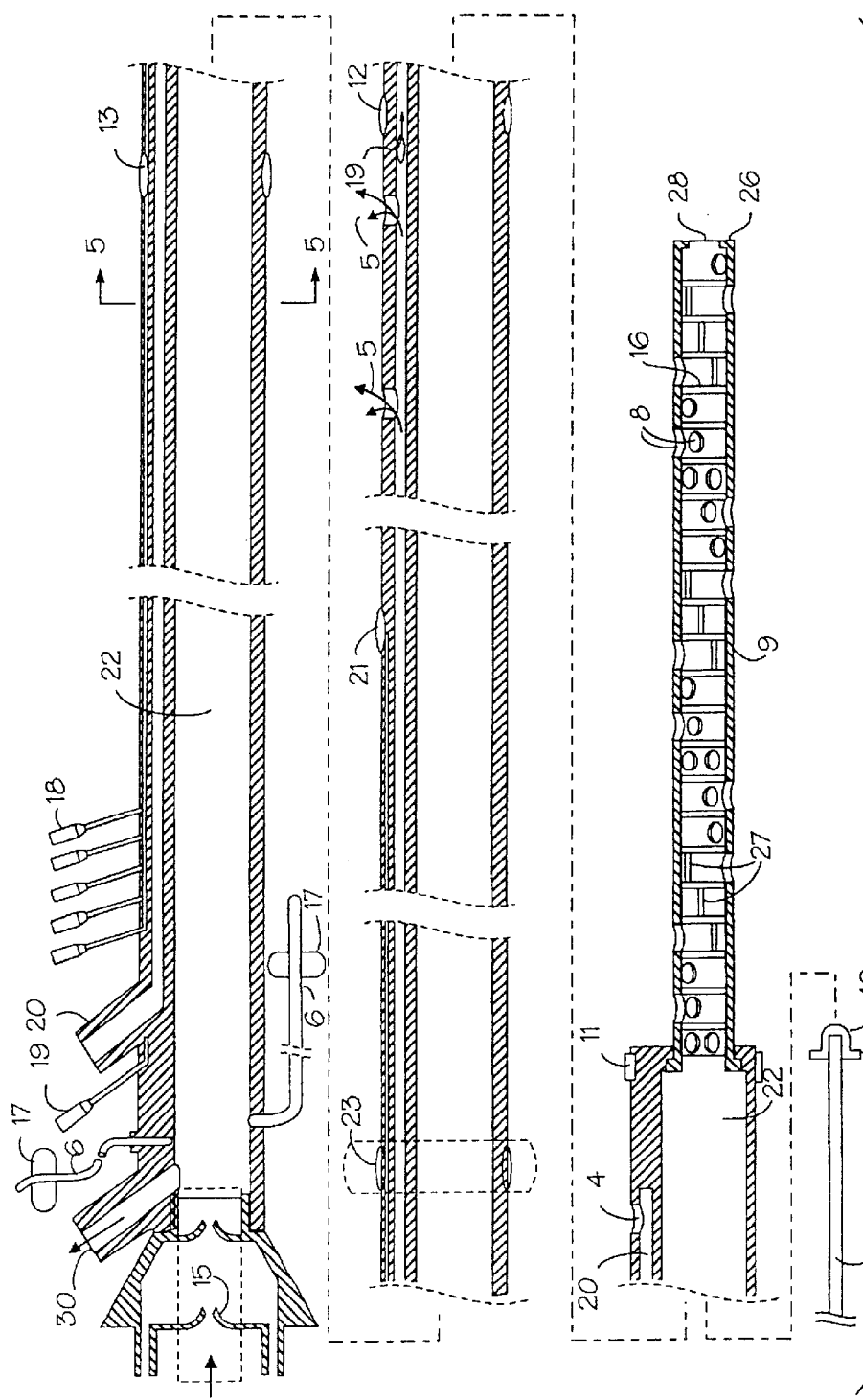
FIG. 1 schematically illustrates a cardiac access catheter system embodying features of the invention.

The catheter system described herein with all of its preferred features represents a versatile system having multiple uses. The catheter is characterized by a flexible catheter shaft placed by surgical cutdown or needle/introducer guidewire technique into the vessels of the lower or upper extremity or neck. Larger internal vessels may also be used.

The catheter may have at least one or two major lumen channels. The major channel is a lumen large enough to carry blood and/or robotic instruments used for surgery and for visualization or other investigatory devices or instrumentation. Minor lumens are used for deploying flow control members. They may also be used where smaller lumens are desired such as for cardioplegia. Although the catheter shaft may be provided with a single lumen for inflation of deployment of the flow control members, it is preferred to provide separate lumens for each flow control member so that their deployment can be controlled separately. The diameter of the catheter will vary depending upon the task to be performed and the size of the individual, but will typically range from about 5 mm to about 35 mm in outside diameter for use in adult humans.

The catheter is preferably constructed of thin walled soft flexible heparin coated polyurethane, polyethylene, polyvinyl chloride, polytetrafluoroethylene or similar durable plastic materials, although other suitable materials may be used. A thin wall construction providing a maximum inner diameter is preferred.

Single and/or double major channel catheters are provided depending upon the situation. A single major channel catheter may be required for use in patients with small vessels or to deploy larger devices for intracardiac surgery. This then requires a separate perfusion catheter in the same circulatory system at a different site (venous or arterial). The double major channel catheter provides access for most goals through a single large artery and/or vein.

In the single channel setting, on the venous side the catheter may access and perfuse the pulmonary artery, or traverse the atrial or ventricular septum through natural or created defects to facilitate robotic surgery. A second single channel catheter may drain the right ventricle and/or atrium back to the blood pump. When the heart is emptied and a bloodless surgical field is created, the distal robotic catheter may be positioned in the pulmonary artery, or enter the right or left ventricle or atrium from the right side for performing intra-arterial or intracardiac surgery often in conjunction with a left sided robotically active complimentary catheter of the invention.

The double channel catheter, which may accomplish the same functional goals, enters only one vein if the vessels are large enough, instead of two veins which would be required in the single channel setting.

The catheter, when placed in the jugular vein, with a limb catheter component extending cranially, in the acute surgical setting, allows segmental isolation and drainage of the brain, and the ability to determine venous oxygen saturation.

Selective deployment of the flow control members allows compartmentalization or isolation of selected portions of the patients cardiovascular system; for example, compartmentalization of the atrium from the vena cave or ventricle and the ventricle from the main pulmonary artery. Selective access to the coronary sinus, the right atrium, ventricle or pulmonary artery is thus facilitated. Perfusion of the pulmonary artery allows the use of a patient's lungs to oxygenate blood, which may eliminate the need for an extra corporeal oxygenator.

On the arterial side the long single or double channel catheter may drain and access the left ventricle and/or left atrium and/or pulmonary veins in a retrograde approach. In the single channel setting a separate arterial catheter may enter the opposite limb artery and be advanced into the ascending aorta for antegrade systemic perfusion.

With the distal robotically active port of the catheter in the left heart, selective deployment of the different flow control members permits isolation or compartmentalization of the ventricle (sub-aortic flow control device) from the coronary circulation, i.e. for administration of cardioplegia (supra-aortic flow control member) which is thus separated from the systemic circulation, which in the setting of hypothermic circulatory arrest may be isolated from the perfused cerebral circulation, by a proximal descending aortic flow control member.

When used for intracardiac surgery on valves, septal defects, intra-cardiac masses, or in the pulmonary circulation, the creation of complete deep hypothermic circulatory arrest ("hypothermic circulatory arrest") may be required to create a bloodless field. In certain situations it will be possible to achieve a bloodless field without hypothermic circulatory arrest by continuing the circulation but isolating blood flow adequately from the cardioplegia-arrested heart and actively aspirating collateral blood flow from the ventricle.

Because there is a proximal flow control member that would be deployable in the proximal descending thoracic aorta, and because the aortic perfusion with this system is antegrade beginning just distal to the coronary arteries, with deployment of a supra-coronary flow control member and a proximal aortic flow control member, a low flow of blood through the aortic perfusion lumen could selectively be used to perfuse the cerebral circulation, during hypothermic circulatory arrest.

Imaging systems may be used to view the heart through the catheter, deployable devices such as heart valves may be passed through the catheter, and robotic instruments, including a scalpel, may be passed into the heart through the distal steering lumen to perform surgery with angioscopic visualization. Jet fluid infusion through the angioscope may clear the bloody field and allows direct visualization. Selective inflation of the flow control members prevents regurgitation of fluid between compartments.

The catheter in its preferred form can be broken down into three major sectional components: (1) the distal floppy reinforced tip component, (2) the proximal component, and (3) the connection component.

1. The distal end. The catheters described here preferably have a distal floppy tip constructed of soft and flexible (floppy), non-kinking, reinforcement ringed, fenestrated, non-thrombogenic, thin-walled, durable synthetic material. The distal tip has at least one fenestration to allow passage of robotic intracardiac surgical devices.

The catheters may be introduced either antegrade or retrograde, through heart valves, preferably by a retractable, fenestrated removable tip guide with a guide wire that will be passed through the steering lumen. The distal component extends proximally to the most distal compartment flow control member. The construction of the distal tip component is to enable multiple 360 degrees rotations and serpentine configurations without kinking the catheter, thus avoiding obstruction to blood flow and allowing robotic steering for intra-cardiac or intra-pulmonary vascular surgery.

The distal component begins at the distal flow control member and preferably has multiple sideholes in the floppy tip for drainage of blood from the left ventricle or atrium or perfusion of blood into the pulmonary artery. A central end hole permits exit of robotic surgical instruments and an angioscope from the drainage/steering lumen.

The most distal compartment flow control member in the left heart prevents regurgitation of fluid or blood from the aorta into the left ventricle, and in the right heart, from the pulmonary artery into the right ventricle. The removable guide will typically have a sliding central flexible wire guide to accurately direct the catheter centrally. The guide and tip may be removed once the catheter is in position.

2. The proximal component. The proximal component of the catheter will typically have flow control members ranging in number from three or more, although fewer flow control members may be used. Perfusion ports will typically be distally located between the most distal and the more proximal compartment flow control members to perfuse the coronary, cerebral sub-circulations through minor lumens. Antegrade systemic circulatory flow is provided by a major single or double channel catheter opening in the ascending aorta.

The catheter will typically have separate minor small lumen port exits between the distal flow control member and the supra-coronary aortic flow control member for coronary artery perfusion.

The number and position of flow control members and number and position of perfusion ports will be chosen based on the size of the individual and the circulatory pattern selected. Infusion of cardioplegia into the coronary arteries may be by accomplished with a separate coronary perfusion port lumen, in the catheter, which can be selectively infused.

In certain embodiments of the double channel design, the two channels can slide independently from each other to optimize positioning of one relative to the other.

In the non-sliding double channel embodiments, an especially ultra-thin wall will exist between the inner and outer lumen, to maximize lumen diameters, yet be strong by virtue of its flat shape supported by the outer walls of the catheter.

When deployed in the left heart, the first more proximal supra-aortic valve flow control member is just proximal to the distal end of the proximal component which occludes the aorta above the coronaries and below the brachiocephalic artery with distal side ports to allow infusion of cardioplegia. Between the most distal compartment flow control member and the first more proximal flow control member, are the side ports for coronary artery access.

The cerebral circulation can be perfused antegrade from the major channel opening into the ascending aorta, during circulatory arrest with inflation of the more distal and supra-coronary aortic flow control members (one above the coronary arteries) and the proximal descending thoracic aorta compartment flow control members.

The addition of a supra-renal flow control member in the descending aorta allows the isolation or compartmentalization of blood flow to the thorax and spinal column.

In the right heart, perfusion of the pulmonary artery may be performed through the distal component lumen, and the right heart is drained by the more proximally located major channel of a double or single major channel catheter. This is the optimal arrangement to support isolated right ventricular failure.

A more proximal compartment flow control member positioned into the inflow of the right atrium allows isolated coronary sinus perfusion, through a minor perfusion lumen, when that flow control member and a flow control member beyond the coronary sinus are inflated.

3. The connection component. The connection component may include a proximal flow control member to prevent leakage from the vessel through which entry is gained.

The connection component will typically have a side perfusion limb from the major perfusion channel which is placed into the entered peripheral artery with its proximal flow control member. When the venous circulation is catheterized, a limb/jugular drainage catheter with flow control member is placed in the distal vessel and drains venous blood into the major venous channel of the catheter.

An access diaphragm sealer built into the connection component is used to place the robotic instruments without air or fluid entry or leakage. The dual diaphragm chambered vascular access port (vascular access port) is constructed of flexible synthetic material with spiral cross and counter cross reinforcement supports in the intravascular component. It may be constructed so that it is inserted within the entry vessel or so that it is a separate component residing outside of the body. A removable semirigid pointed inner guide with guide wire lumen, can be used for percutaneous or open vascular placement. The vascular access port preferably has four features: (1) an outer soft diaphragm with self-sealing penetratable center opening, (2) an inner soft diaphragm of similar construction, (3) an aspiration port from the chamber between the diaphragms, and (4) a fluid infusion port into the chamber.

The chamber acts as an air lock and washout lock which is necessary when introducing large devices into the vascular system to prevent air embolization and fluid leakage. It minimizes trauma from repeated entries of large devices. The vascular access port can be directly inserted into a vessel to allow passage of robotic instruments or intravascular devices.

The vascular access port is designed also as the access port component of the outside connection component of a system as described here.

The ports for the minor lumens for perfusion of a compartment between flow control members or to fluid inflate the flow control members, are located outside the vessel entered as part of the connection component.

The major attributes of the system with its preferred embodiments are its ultrathin walled, flexible reinforced non-kinking double and/or single major channel catheters with inflatable/deflatable flow control members which compartmentalize the circulatory system into sub-circulatory systems to specifically include coronary, cerebral and limb or neck peripheral access vessels. Minor lumen are used for flow control member inflation/deflation control.

Entry site limb catheters allow drainage or perfusion of the vessel entered to permit continual placement of the catheter for several days, if necessary for subacute cardiac assist, to protect the limb vasculature entered. This also permits metabolic monitoring access to that limb or cerebral circulation, in the case of neck vessels accessed.

Implementation

The system also achieves complete decompression (by direct drainage) of either or both ventricles. Further, active or passive return of the intra-cardiac blood to a blood pump of unoxygenated blood (directly from the right ventricle) or oxygen enriched blood (directly from the left ventricle) is achieved along with antegrade perfusion of the pulmonary artery or aorta. The blood at the system level of the pump may or may not require oxygen enrichment. The described compartment flow control members prevent catheter migration and regurgitant blood/fluid flow between compartments. This may be used to improve the creation of a bloodless surgical field in the heart chamber to be operated on. It also permits selective perfusion or drainage of a selected sub-circulatory system, i.e. the brain, lungs, thorax, heart or limb.

A catheter system is contemplated herein that includes multiple catheters as described which differ from each other in their outside diameters. The catheter system may further contain multiple catheters that have flow control members in varying positions from which a selection can be made depending upon the task to be performed and the patient's needs.

The catheter system can be further explained with reference to the accompanying figures, wherein like numbers reference like elements:

FIG. 1 depicts elements of a catheter system as described herein. At the distal end of the catheter is a removable and retractable catheter guide (10) which has at least one fenestration (88) to permit fluids to pass through the catheter as it moves through the body. The guide may be retracted from the catheter when desired by simply pulling out the guide by the retractor rod (24). Typically this is done when the catheter is in place within the heart. A bullet shape for the guide is preferred and allows for less traumatic penetration across the heart valves or narrowings. A lip (25) is provided on the guide to match a ledge (26) at the end of the catheter tip. The ledge (26) catches the lip (25) so that the guide will pull the catheter system through the body. The floppy tip (9) through which the catheter guide slides extends from the open end steering robotic channel (22) to the distal compartment flow control member (11).

Figure 2:
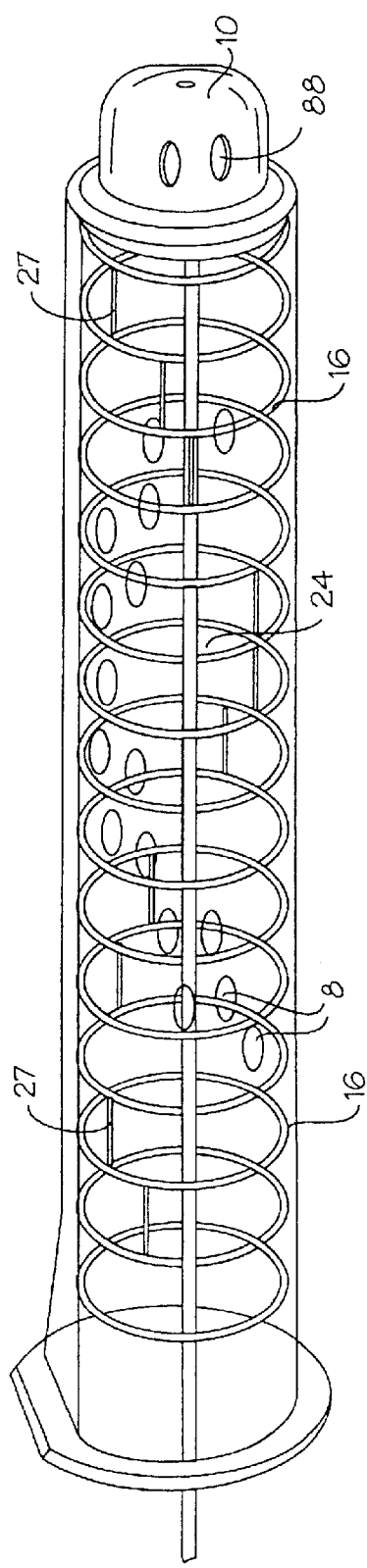
FIG. 2 illustrates the preferred fenestrated floppy tip and fenestrated removable catheter guide.

The floppy tip preferably has multiple circumferential ring members (16) which w support the catheter shaft and multiple fenestrations (8) placed between various ring members which allow fluid flow through the catheter. The ring members are held together and further supported by a support strut (27) bridging two consecutive rings. It is preferred that the support struts be placed perpendicular to the rings and be arranged randomly or distant from each other around the circumference of the tip. The floppy tip and the removable catheter guide are illustrated in more detail in FIG. 2.

At the proximal end of the floppy tip (9) is the open end steering robotic channel (22). There is a distal flow control member (11) near the distal end of the lumen and just proximal to the floppy tip. Useable flow control members include, but are not limited to, expandable or inflatable members such as an inflatable balloons and collapsible/deployable valves of various configurations including retrograde valves, antegrade valves, and various central flow and peripheral flow valves. A combination of valves and inflatable members may be used as appropriate for a given procedure, thus In some embodiments, the catheter body can include one or more antegrade and retrograde valves, as well as one or more inflatable balloons. The flow control members will typically surround the catheter shaft circumferentially, particularly when expanded or deployed. Proximal to the distal flow control member (11) is a perfusion fenstration or port (4), which typically will be in fluid connection with the coronary artery or sinus limb through a channel (20). Aortic perfusion ports (5) are located just proximal to the aortic flow control member (12). A channel (20) for these ports provides fluid connection along the course of the catheter. For example, the blood channel (20) provides a means to carry blood to and from the aorta. Minor lumens can be used to infuse cardioplegia, as desired. These ports (5) provide a path through which blood may be returned to the patient in the aorta, or drained from the right heart in the opposite direction. One optional embodiment of the catheter described herein omits the presence of the proximal component channel (20).

Other flow control members (12), (23), (13) and (17) are positioned along the catheter and proximal to the distal flow control member (11). In one preferred embodiment, one or more flow control members comprise an inflatable balloon or equivalent. The inflatable balloon may be made of a highly elastic material, such as flexible polymers or elastomers, which include but are not limited to latex, silicone rubber, polyurethane, polyvinylchloride, polyethylene, polypropylene, polyamides, polyesters, and alloys, copolymers, and reinforced composites thereof. The balloon, when inflated, may assume a spherical, toroidal or cylindrical shape. When deflated, the balloon preferably conforms closely to the exterior of the catheter shaft for unobstructed insertion at the entry site. Each such flow control member has an interior which is in fluid communication with an inflation lumen extending within the catheter shaft from a location within the respective flow control member to a port (18) in the proximal portion which is adapted to extend out of the patient. It is preferred that flow control members be positioned along the catheter shaft such that after the catheter has been positioned in the patient's body, a first flow control member is located at the proximal end of the catheter shaft at or near the site of entry of the shaft into the patient, a second flow control member is located distal to the first flow control member which is dimensioned and configured so that it may sit in the proximal descending thoracic aorta, a third flow control member distal to the second flow control member is dimensioned and configured so that it may sit between the coronary ostia and the brachiocephalic artery and a fourth flow control member distal to the third flow control member is dimensioned and configured so that it may sit in the left ventricular outflow tract. A proximal descending thoracic aortic flow control member such as one analogous to that of the flow control member (12) allows compartmentalization of the cerebral circulation between that and a coronary flow control member such as one analogous to that of the flow control member (4). Perfusion from the aortic perfusion channel (20) allows selective cerebral perfusion during deep hypothermic circulatory arrest. Flow control member ports (18) may be provided which allow further selective inflation or deflation of compartment flow control members.

Limb drainage (venous) (6) or perfusion (arterial) (6) with compartment flow control members (17), may be used for longer surgical procedures.

The diaphragmed entry port (14) is at the most proximal end of the catheter, has a self-sealing dual diaphragm (15) and provides for catheter steering and entry of robotic instruments. The entry port (14) has entrance and exit ports (29) through which fluid can be permitted to flow through the entry port primarily to flush air out of the port after the robotic instruments are placed into the entry port. Typically a lumen branch (30) will be provided to permit flow of fluids from the catheter to be diverted away from the entry port.

Figure 3:
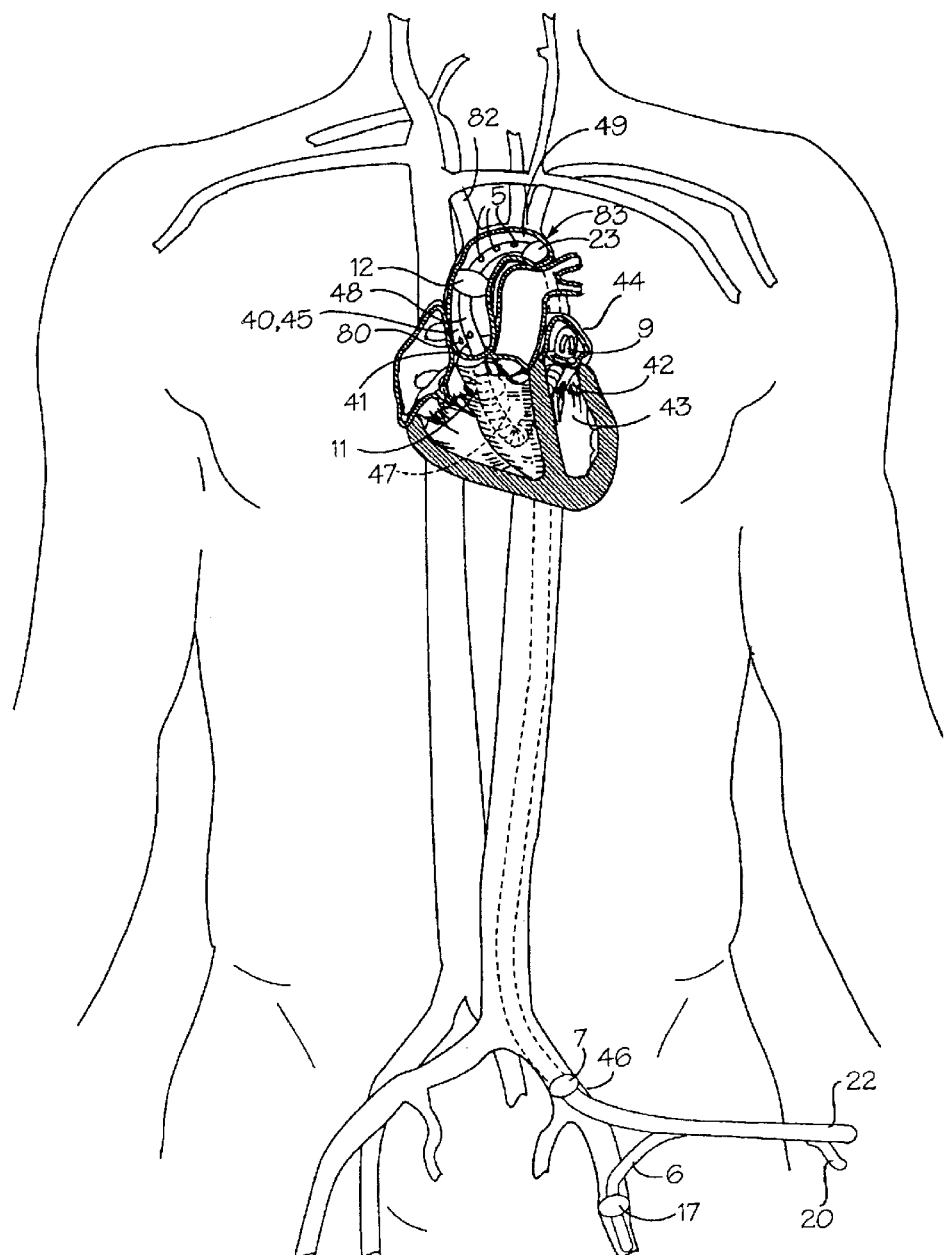
FIG. 3 illustrates a system as placed into the left heart by entering a single iliac artery with the flow control members comprising inflatable balloons.

FIG. 3 illustrates a system as placed into the left heart by entering an iliac artery, wherein the flow control members comprise inflatable balloons. The fenestrated floppy tip (9) is illustrated traversing the aortic (41) and mitral valve (42) to place the open robotic channel (22) in the left heart chambers (i.e. the left atrium 44 and the left ventricle 43). The distal seating flow control member (11) sits in the left ventricular outflow tract (47) to prevent fluid from above the aortic valve (41) from entering the left ventricle (43). The coronary perfusion lumen (48) between the distal (11) and the ascending aortic flow control member (12) is positioned between the coronary ostia (80) and the brachiocephalic artery (82) to infuse the two coronary ostia (80) by flooding the ascending aorta (40), between the flow control members or just above the aortic valve. A flow control member (23) sits in the proximal descending thoracic aorta (83). The aortic perfusion ports (5) sit in the ascending aorta (45) and aortic arch (49) to provide antegrade blood flow in the majority of the aorta. The entry site is into the iliac artery (46) with the connecting components outside the artery. The seating flow control member (7) on the main catheter inside the iliac artery (46), and (17) on the distal limb perfusion catheter (6) is also shown.

If one catheter is used to enter each iliac artery to access the left heart, one catheter traverses the iliac artery to the left heart chamber. This enables placement of a larger single channel catheter for robotic procedures in the opposite iliac artery, but necessitates a contralateral arterial perfusion catheter.

Figure 4:
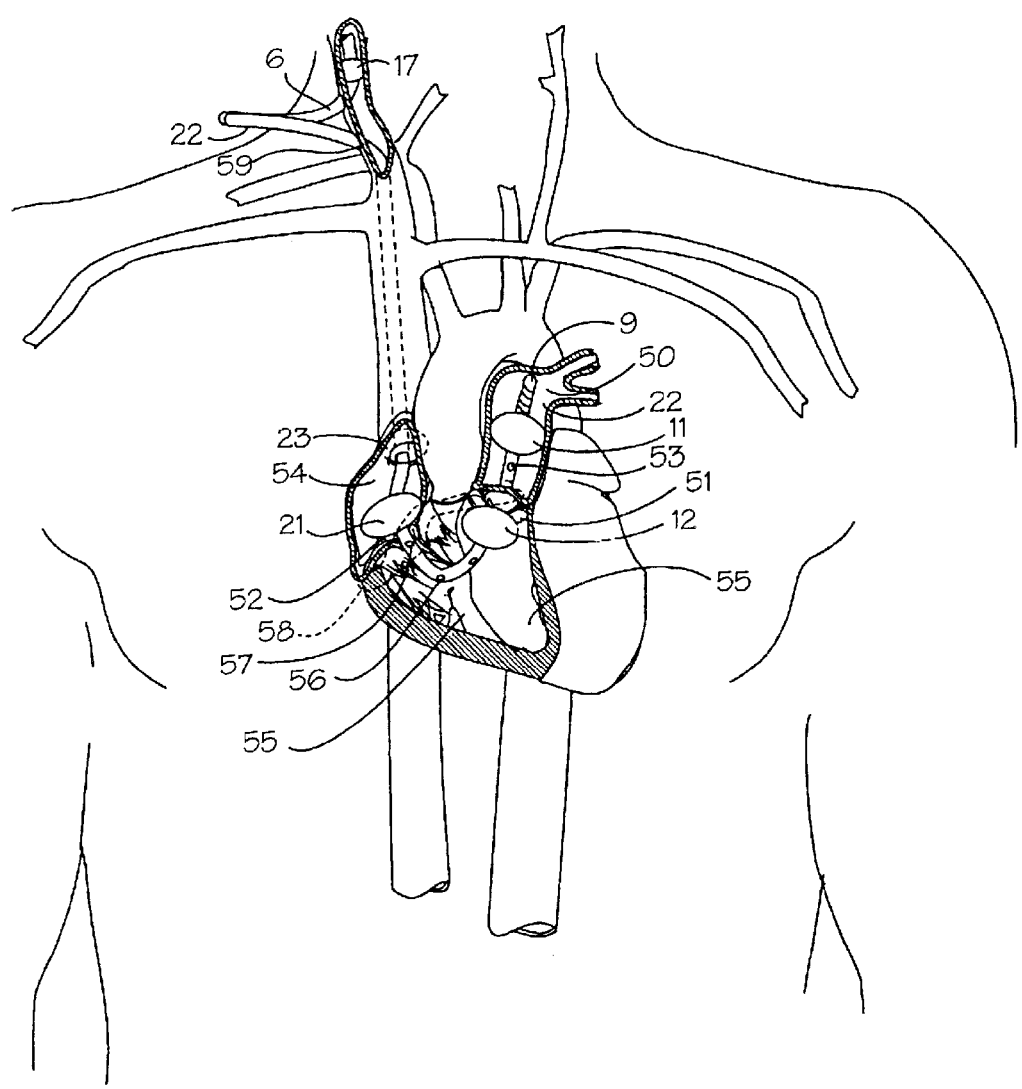
FIG. 4 illustrates a system as placed in the right heart by entering the jugular vein with the flow control members comprising inflatable balloons.

FIG. 4 illustrates a system in the right heart entering a single vein, wherein the flow control members comprise inflatable balloons. The distal floppy tip component (9) of the catheter is placed in the main pulmonary artery (50) after having traversed the tricuspid (52) and pulmonic valves (51). In this position the major distal channel (22) may perfuse the pulmonary artery (50) or provide robotic access to the right heart (right atrium 54 and right ventricle 55). The distal seating flow control member (11) prevents regurgitation of blood into the right heart. The proximal drainage ports (56), which are positioned in the right ventricle (55), communicate with the outer proximal channel (20, FIG. 1) to drain blood from the right heart to the outside. A seating flow control member (23), at the opening of the right atrium (54) prevents regurgitation of fluid from the right atrium (54). The coronary sinus perfusion port (57) is shown near the coronary sinus (58). A flow control member (12) seats the catheter in position just below the pulmonic valve (53) and another flow control member (21) seats the catheter in position at the coronary sinus. The major channel (22) enters the jugular vein (59) and a limb catheter (6) seated by a flow control member (17) drains the occluded vein proximally.

If two separate veins are used to enter the right heart, a single channel catheter may be used to enter the jugular vein to access the pulmonary artery and right heart with the floppy tip. The single channel will allow a larger catheter for robotic surgery. Another single channel catheter could be used to enter the iliac vein to enter the right heart for drainage. Preferably a limb catheter with a seating flow control member would be used to drain the distal limb.

Figure 5:
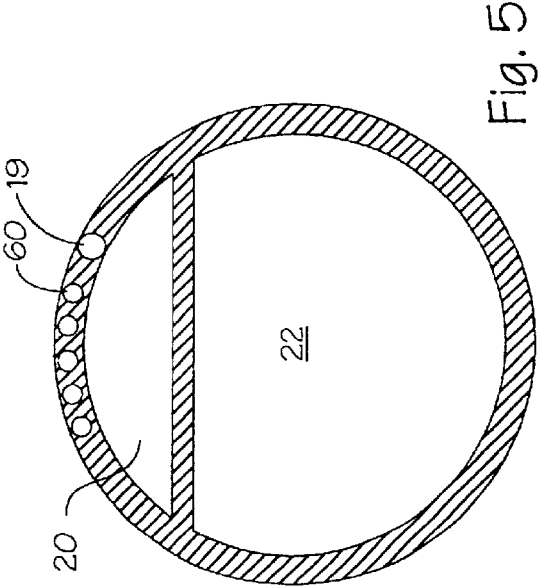
FIG. 5 illustrates a cross section of the catheter depicted in FIG. 1, taken along line 1—1 in FIG. 1.

FIG. 5 shows a cross section of the double major channel and multiple minor lumen construction taken long the line 5—5 in FIG. 1. The major channel (22) allows for placement of instruments and robotic instruments and has an outer thin wall which separates it from another major, but smaller channel (20). Minor lumen (19) and channel (20) permit the inflow and outflow of fluids as required for the particular surgery and minor lumens (60) permit the fluid connection for inflation of the flow control members. The minor lumens are primarily used as perfusion lumens.

Figure 6:
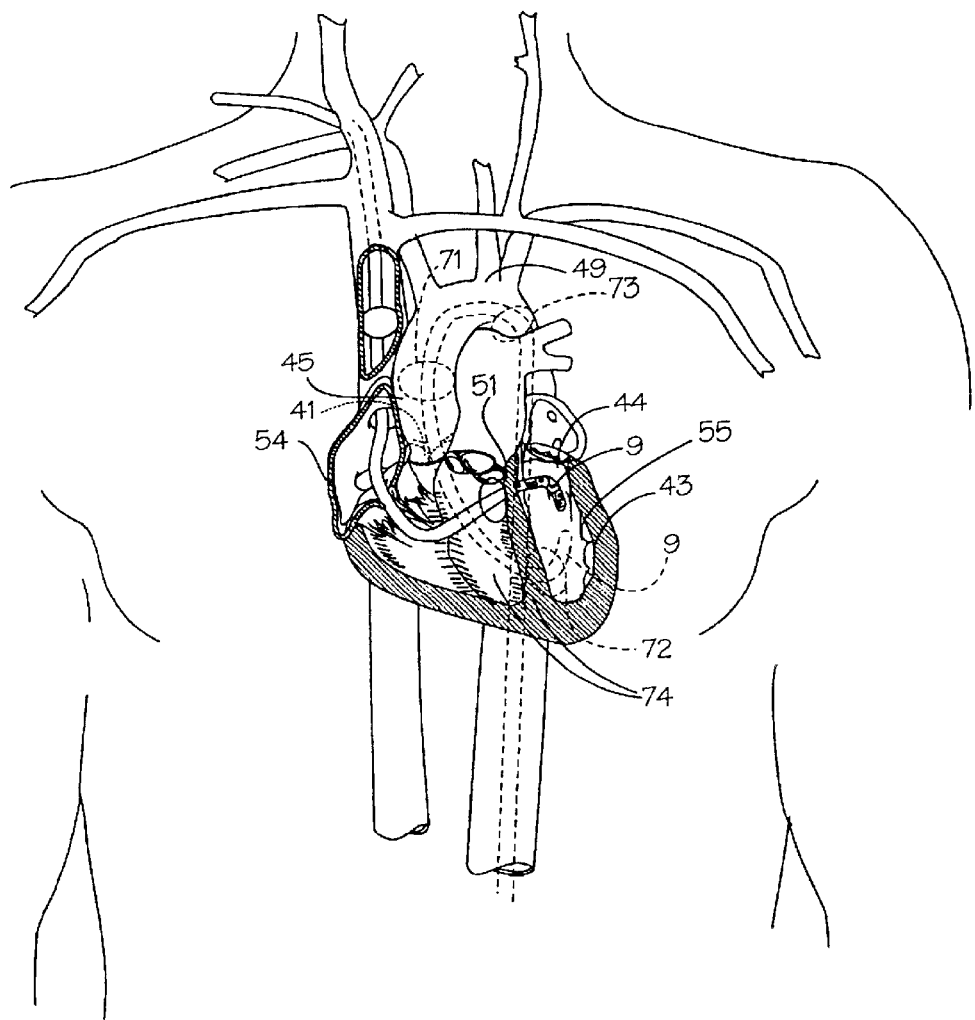
FIG. 6 illustrates a catheter system showing transeptal complimentary catheters.

FIG. 6 illustrates a system showing transeptal complimentary catheters, wherein the flow control members comprise inflatable balloons. An exemplary method of performing biventricular robotic transeptal surgery on intracardiac structures and achieving deep hypothermic circulatory arrest is as follows:

A. The distal end component (9) of the catheter system is advanced to a location inside the left heart by peripheral vascular entry, which by way of specifically designed catheters traverses the aortic valve (41) with a retractable guide, and provides access for specifically designed instruments and robotic instruments, and angioscopic or other imaging catheters to enter the inner chambers of the left heart through the aortic valve (41).

B. A major channel is used to empty the left ventricle (43) into a blood reservoir through its blood channel, then to be pumped back through the more proximally terminating blood channel into the aortic arch (49) while the blood is oxygen enriched and cooled to achieve hypothermic circulatory arrest. One flow control member is inflated to seat the catheter in the entry vessel and the distal flow control member (71) is inflated to prevent regurgitant flow from the aorta into the left heart.

C. Simultaneously, a catheter is advanced through a peripheral vein into the right heart with the distal component end placed in the right atrium and advanced across the septum into the left atrium (44). The more proximal blood channel ends in the right atrium. Blood is drained from both channels into the blood reservoir to be cooled, oxygen-enriched and pumped back to the patient through the proximal ascending aortic blood channel.

D. Once the patient is sufficiently cooled, a proximal descending thoracic aortic flow control member (72) is inflated and a proximal ascending aortic flow control member (71) are inflated to allow low flow selective perfusion of the aortic arch vessels while the body is otherwise emptied of blood to create a bloodless surgical field.

E. With circulatory arrest, the proximal channel of the venous catheter drains blood from the right heart returning from perfusing the brain. The distal tip component (9) of the right heart catheter can be positioned across the atrial septum (74) or into the left ventricle (55) for dual left heart access concurrently with the left ventricular catheter advanced from the aorta end component. Access may be had to all intracardiac structures from either side of the structure including all four heart valves and both atrial and ventricular septal defects simultaneously from the right and left heart vantages thus enabling complimentary actions on either side of the surgical target. If a septal defect is not congenitally present and transeptal access is needed, a robotic scalpel is used to create such a defect.

F. Upon completion of surgery, the proximal ascending and proximal descending thoracic aortic flow control members are deflated and full blood flow is reestablished as at the outset of the procedure until the patient is fully rewarmed and weaned off of cardiopulmonary bypass.

G. Should a patient require prolonged mechanical support, the catheters are advanced as described above with the right heart catheter having its tip in the pulmonary artery. If isolated right heart bypass is elected the blood is drained from the proximal intracardiac blood channel and oxygenated (optional) blood is pumped back into the pulmonary artery through the distal channel. If complete biventricular bypass is required both the blood channels of the right heart catheter drain blood back to the heart pump, where it is oxygenated and pumped back into the ascending aortic component.

H. For left heart support the distal end component of the left heart catheter is advanced into the left ventricle and blood is drained from that channel back to the blood pump reservoir and oxygen enriched (optional) and pumped back through the proximal ascending aortic channel with or without the blood drained from the right heart.

The above method allows a traumatic prolonged presence of the distal end component in the heart while the right or left or both heart(s) is (are) beating and being mechanically supported.

In another embodiment, various kinds of valves may be used in addition to, or instead of one or more of the inflatable balloons described previously. Useable valves include collapsible/expandable valves of various configurations including retrograde valves and antegrade valves, used as appropriate, and various central flow and peripheral flow valves. Descriptions of suitable flow control valves may be found in the Mackoviak Ross patents which have already been incorporated herein by reference (U.S. patent application Ser. No. 08/664,361, filed Jun. 17, 1996, by John A. Macoviak and Michael Ross; U.S. patent application Ser. No. 08/664,360, filed Jun. 17, 1996, by John A. Macoviak and Michael Ross).

Figure 7:
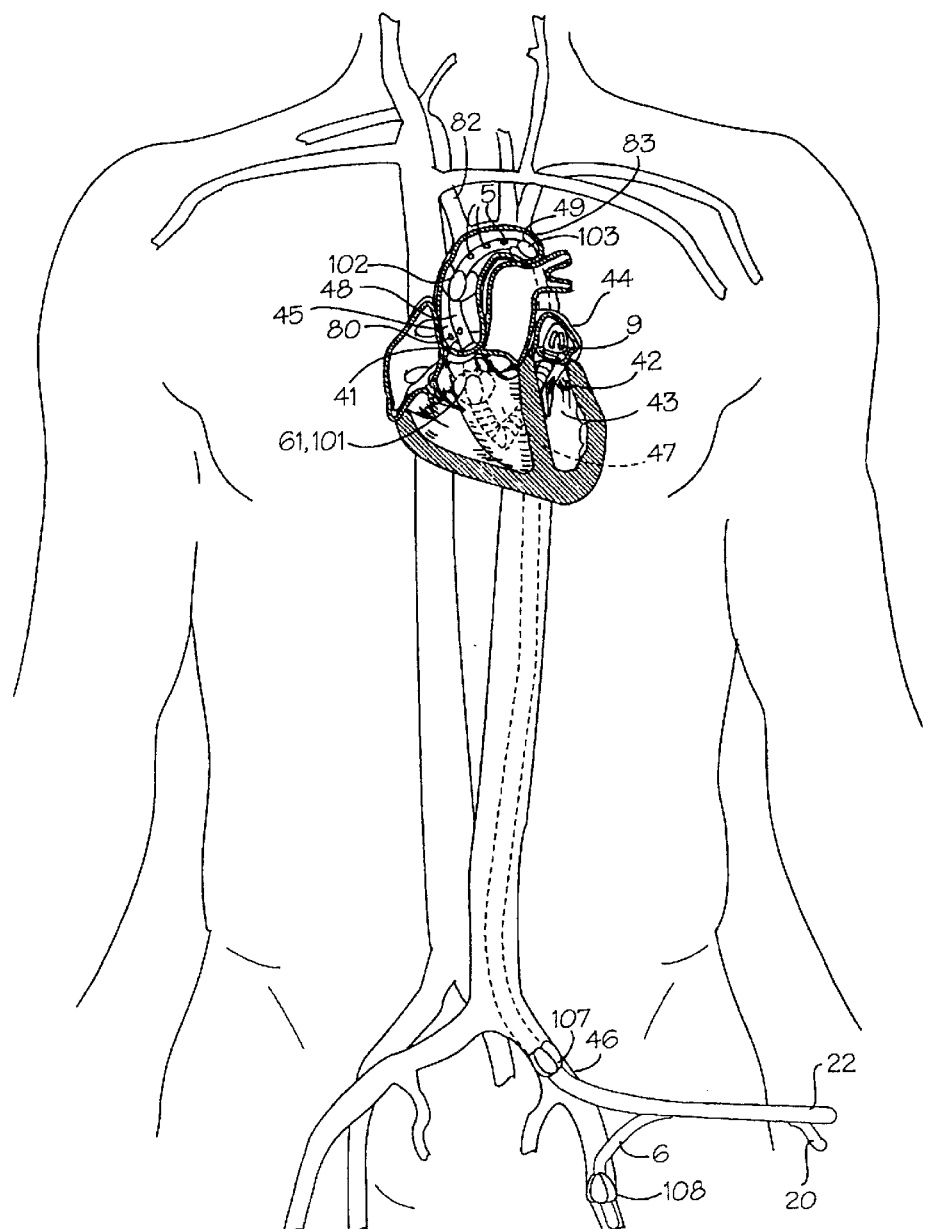
FIG. 7 illustrates the system of FIG. 3 as placed into the left heart by entering an iliac artery, but with the flow control members comprising flow control valves.

FIG. 7 illustrates the system placed into the left heart by entering a single iliac artery as described in FIG. 3, except that the flow control members comprise valves as opposed to the inflatable balloons previously discussed. Like numbers are used to denote like features. The fenestrated floppy tip (9) is illustrated traversing the aortic (41) and mitral valve (42) to place the open robotic channel (22) in the left heart chambers (i.e. the left atrium 44, and left ventricle 43). The distal antegrade flow control valve (61) sits in the left ventricular outflow tract (47) to prevent fluid from above the aortic valve (41) from entering the left ventricle (43). The coronary perfusion lumen (48) between the distal seating flow control member (101) and the ascending aortic antegrade flow control valve (102) is positioned between the coronary ostia (80) and the brachiocephalic artery (82) to infuse the two coronary ostia (80) by flooding the ascending aorta (40), between the flow control members or just above the aortic valve. A proximal aortic antegrade flow control valve (103) sits in the proximal descending thoracic aorta (83).

The aortic perfusion ports (5) sit in the ascending aorta (45) and aortic arch (49) to provide antegrade blood flow in the majority of the aorta. The entry site is into the iliac artery (46) with the connecting components outside the artery. The retrograde flow control valve (107) on the main catheter inside the iliac artery (46), and antegrade flow control valve (108) on the distal limb perfusion catheter (6), are also shown.

If one catheter is used to enter each iliac artery to access the left heart, one catheter traverses the iliac artery to the left heart chamber. This enables placement of a larger single channel catheter for robotic procedures in the opposite iliac artery, but necessitates a contralateral arterial perfusion catheter.

Figure 8:
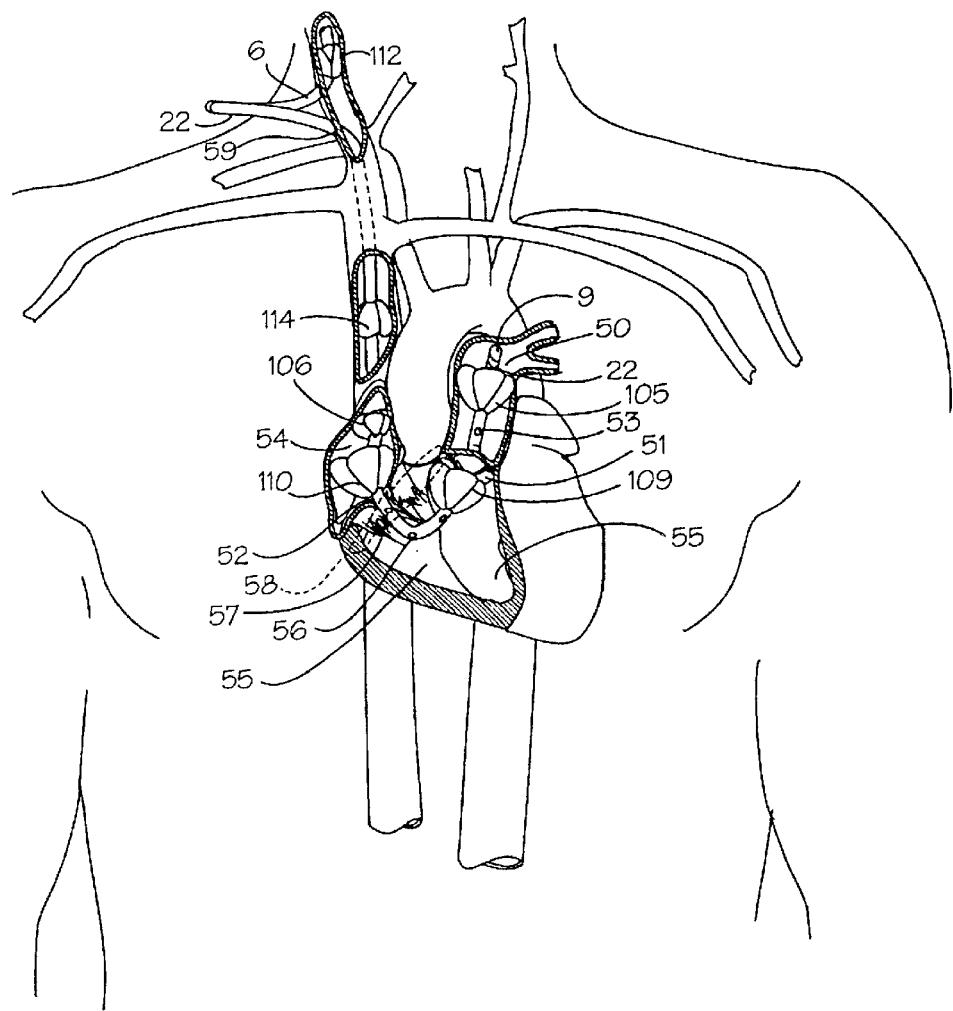
FIG. 8 illustrates the system of FIG. 4 as placed in the right heart by entering the jugular vein with the flow control members comprising flow control valves.

FIG. 8 illustrates a system, wherein the flow control members comprise flow control valves, in the right heart entering a single vein. The distal floppy tip component (9) of the catheter is placed in the main pulmonary artery (50) after having traversed the tricuspid (52) and pulmonic valves (51). In this position the major distal channel (22) may perfuse the pulmonary artery (50) or provide robotic access to the right heart (right atrium 54, and right ventricle 55). The distal antegrade flow control valve (105) prevents regurgitation of blood into the right heart. The proximal drainage ports (56), which are positioned in the right ventricle (55), communicate with the outer proximal channel (20, FIG.1) to drain blood from the right heart to the outside. A retrograde flow control valve (106), at the opening of the right atrium (54) prevents regurgitation of fluid from the right atrium (54). The coronary sinus perfusion port (57) is shown near the coronary sinus (58). A flow control member (109) seats the catheter in position just below the pulmonic valve (53) and a retrograde flow control valve (110) seats the catheter in position at the coronary sinus. The major channel (22) enters the jugular vein (59) seated by the antegrade flow control valve (114). Limb catheter (6) also enters the jugular vein (59) and is seated by a retrograde flow control member (112) drains the occluded vein proximally.

If two separate veins are used to enter the right heart, a single channel catheter may be used to enter the jugular vein to access the pulmonary artery and right heart with the floppy tip. The single channel will allow a larger catheter for robotic surgery. Another single channel catheter could be used to enter the iliac vein to enter the right heart for drainage. Preferably a limb catheter with a seating flow control member would be used to drain the distal limb.

Figure 9:
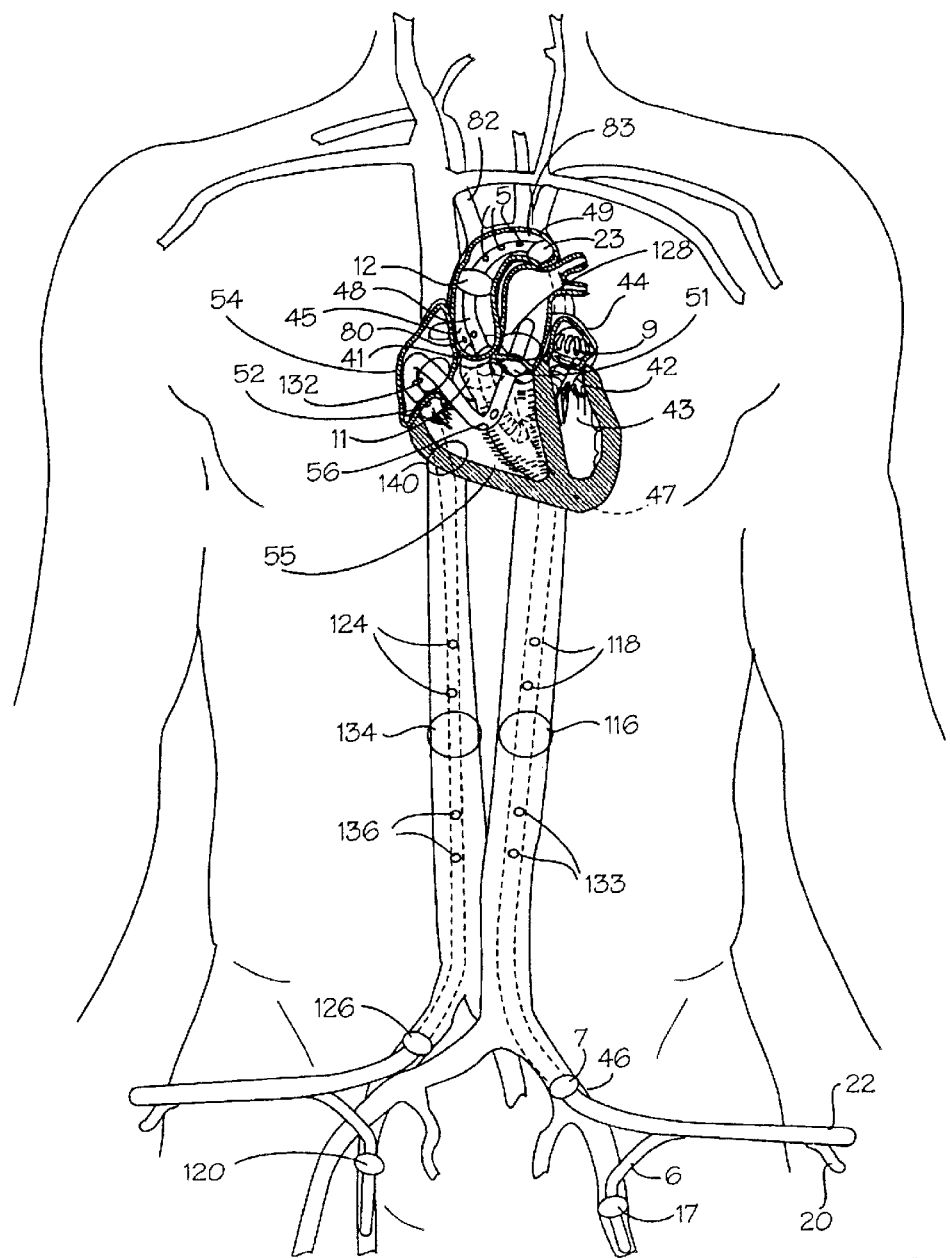
FIG. 9 illustrates the system of FIG. 7 as placed into the left heart through an iliac artery, and a second device placed into the right heart through an iliac vein.

FIG. 9 illustrates a catheter of the invention placed into the left heart by entering a single iliac artery as described in FIG. 3, and a catheter placed into the right heart by entering an iliac vein. The description of the catheter in the left heart is exactly as described in FIG. 3, except that a supra-renal inflatable flow control member (116) is positioned in the descending aorta. The fenestrated floppy tip (9) is illustrated traversing the aortic (41) and mitral valve (42) to place the open robotic channel (22) in the left heart chambers (i.e. the left atrium 44 and the left ventricle 43). The distal seating flow control member (11) sits in the left ventricular outflow tract (47) to prevent fluid from above the aortic valve (41) from entering the left ventricle (43). The coronary perfusion lumen (48) between the distal (11) and the ascending aortic flow control member (12) is positioned between the coronary ostia (80) and the brachiocephalic artery (82) to infuse the two coronary ostia (80) by flooding the ascending aorta (40), between the flow control members or just above the aortic valve. A flow control member (23) sits in the proximal descending thoracic aorta (83). The aortic perfusion fenstrations or ports (5) sit in the ascending aorta (45) and aortic arch (49) to provide antegrade blood flow in the majority of the aorta. The entry site is into the iliac artery (46) with the connecting components outside the artery. The seating flow control member (7) on the main catheter inside the iliac artery (46), and (17) on the distal limb perfusion catheter (6) is also shown. The supra-renal flow control member (116) is positioned below the aortic branches which feed the thorax and spinal column. Perfusion ports (118) allow isolated perfusion of the thorax and spinal column. The fenstrations or ports (138) are for perfusing the renal arteries.

The right heart catheter enters the heart as shown in FIG. 4 except that the entry point to the body is through an iliac vein, and a supra-renal flow control member (134) is positioned below the azygos veins. The distal floppy tip component (9) of the catheter is placed in the main pulmonary artery (50) after having traversed the tricuspid (52) and pulmonic valves (51). In this position the major distal channel (22) may perfuse the pulmonary artery (50) or provide robotic access to the right heart (right atrium 54 and right ventricle 55). The distal seating flow control member (128) prevents regurgitation of blood into the right heart. The proximal drainage ports (56), which are positioned in the right ventricle (55), communicate with the outer proximal channel (20, FIG. 1) to drain blood from the right heart to the outside. A seating flow control member (23), at the opening of the right atrium (54) prevents regurgitation of fluid from the right atrium (54). The coronary sinus perfusion port (57) is shown near the coronary sinus (58). A flow control member (130) seats the catheter in position just below the pulmonic valve (53) and another flow control member (132) seats the catheter in position at the coronary sinus. The major channel (22) enters the iliac vein seated by flow control member (126). Limb catheter (6) also enters the iliac vein and is seated by a flow control member (120) which drains the occluded vein proximally. Fenstrations or ports (124) allow the compartmentalized return of the fluid used to perfuse the thorax and spinal column. Fenstrations or ports (122) allow drainage of the right atrium. The fenstrations or ports (136) are for draining the renal veins.

In an alternate embodiment of the catheter system seen in FIG. 9, an additional flow control member (140) may be positioned above the azygos veins to more precisely isolate the azygos veins.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A biventricular vascular catheter for providing access to a patient's heart for cardiopulmonary surgery, for cardiopulmonary circulatory support, and for circulatory arrest of the heart comprising:
    (a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration; and
    (b) a succession of flow control members positioned along the catheter shaft such that after the catheter has been positioned in the patient's body, at least one of the flow control members is positioned within the patient's heart and at least one subcirculation region within the patient is isolated, wherein such subcirculation region is selected from the group consisting of the coronary arterial, cerebral, pulmonary, neck and limb spinal and thoracic subcirculations.

2. The catheter of claim 1, wherein the elongated catheter shaft is configured to be advanceable across a septum between chambers of the heart.

3. The catheter of claim 1, wherein the catheter further comprises means for draining one or more chambers of the heart.

4. The catheter of claim 1, wherein the flow control members comprise inflatable balloons.

5. The catheter of claim 4, wherein the inflatable balloons are independently inflatable.

6. The catheter of claim 1, wherein the catheter accommodates the selective perfusion or drainage of blood either separately or at the same time.

7. A biventricular vascular catheter for providing access to a patient's heart for cardiopulmonary surgery, for cardiopulmonary circulatory support, and for circulatory arrest of the heart comprising:
    (a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration; and
    (b) a succession of flow control members positioned along the catheter shaft such that after the catheter has been positioned in the patient's body, at least one of the flow control members is positioned within the patient's heart and at least one subcirculation region within the patient is isolated, wherein the succession of flow control members comprises at least two flow control members which are positioned along the catheter shaft at desired locations to isolate circulation to the thorax and spinal column.

8. A biventricular vascular catheter for providing access to a patient's heart for cardiopulmonary surgery, for cardiopulmonary circulatory support, and for circulatory arrest of the heart comprising:
    (a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration: and
    (b) a succession of flow control members positioned along the catheter shaft such that after the catheter has been positioned in the patient's body, at least one of the flow control members is positioned within the patient's heart and at least one subcirculation region within the patient is isolated, wherein the succession of flow control members comprises at least two flow control members which are positioned along the catheter shaft at desired locations to isolate drainage of the azygous veins.

9. A biventricular vascular catheter for providing access to a patient's heart for cardiopulmonary surgery, for cardiopulmonary circulatory support, and for circulatory arrest of the heart comprising:
    (a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestrations
    (b) a succession of flow control members positioned along the catheter shaft such that after the catheter has been positioned in the patient's body, at least one of the flow control members is positioned within the patient's heart and at least one subcirculation region within the patient is isolated; and
    c) means for perfusing the pulmonary artery.

10. A biventricular vascular catheter for providing access to a patient's heart for cardiopulmonary surgery, for cardiopulmonary circulatory support, and for circulatory arrest of the heart comprising:
    (a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration;

(b) a succession of flow control members positioned along the catheter shaft such that after the catheter has been positioned in the patient's body, at least one of the flow control members is positioned within the patient's heart and at least one subcirculation region within the patient is isolated; and (c) means for perfusing the pulmonary artery and means for draining one or more chambers of the heart.

11. A biventricular vascular catheter for providing access to a patient's heart for cardiopulmonary surgery, for cardiopulmonary circulatory support, and for circulatory arrest of the heart comprising:

(a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration; and (b) a succession of flow control members positioned along the catheter shaft such that after the catheter has been positioned in the patient's body, one or more of the flow control members are positioned within the patient's heart, and wherein the succession of flow control members comprises at least two flow control members which are positioned along the catheter shaft at desired locations to isolate subcirculation regions within the patient, wherein such subcirculation region is selected from the group consisting of the coronary arterial, cerebral, pulmonary, neck and limb, spinal and thoracic subcirculations.

12. The catheter of claim 11, wherein the elongated catheter shaft is configured to be advanceable from a peripheral vessel to and through two or more chambers of the heart including across a septum between chambers.

13. The catheter of claim 11, further comprising a first inner channel extending therein from a port in the distal end of the shaft to a location in the proximal end.

14. The catheter of claim 11, wherein the catheter further comprises means for draining, at least one chamber of the heart.

15. The catheter of claim 11, wherein the succession of flow control members includes one or more flow control members comprising an inflatable balloon.

16. The catheter of claim 15, wherein the one or more inflatable balloons are independently inflatable.

17. A biventricular vascular catheter for providing access to a patient's heart for cardiopulmonary surgery, for cardiopulmonary circulatory support, and for circulatory arrest of the heart comprising:

(a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration;

(b) a succession of flow control members positioned along the catheter shaft such that after the catheter has been positioned in the patient's body, one or more of the flow control members are positioned within the patient's heart, and wherein the succession of flow control members comprises at least two flow control members which are positioned along the catheter shaft at desired locations to isolate subcirculation regions within the patient, wherein the succession of flow control members comprises a first expandable member located at the proximal end of the catheter shaft at the site of entry of the shaft into the patient; and (c) a first inner channel extending therein from a port in the distal end of the shaft to a location in the proximal end.

18. The catheter of claim 17, wherein the succession of flow control members comprises a second flow control member located distal to the first flow control member, and which is dimensioned and configured so that it seats in the proximal descending thoracic aorta.

19. The catheter of claim 18, wherein the succession of flow control members comprises a third flow control member, distal to the second flow control member, which is dimensioned and configured so that is seats between the coronary ostia and the brachiocephalic artery.

20. A biventricular vascular catheter for providing access to a patient's heart for cardiopulmonary surgery, for cardiopulmonary circulatory support, and for circulatory arrest of the heart comprising:

(a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration; and (b) a succession of flow control members positioned along the catheter shaft such that after the catheter has been positioned in the patient's body, one or more of the flow control members are positioned within the patient's heart, and wherein the succession of flow control members comprises at least two flow control members which are positioned along the catheter shaft at desired locations to isolate subcirculation regions within the patient, wherein the succession of flow control members comprises at least two flow control members which are positioned along the catheter shaft at desired locations to isolate circulation to the thorax and spinal column.

21. A biventricular vascular catheter for providing access to a patient's heart for cardiopulmonary surgery, for cardiopulmonary circulatory support, and for circulatory arrest of the heart comprising:

(a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration;

(b) a succession of flow control members positioned along the catheter shaft such that after the catheter has been positioned in the patient's body, one or more of the flow control members are positioned within the patient's heart, and wherein the succession of flow control members comprises at least two flow control members which are positioned along the catheter shaft at desired locations to isolate subcirculation regions within the patient; and (c) means for perfusing the pulmonary artery.

22. A biventricular vascular catheter for providing access to a patient's heart for cardiopulmonary surgery, for cardiopulmonary circulatory support, and for circulatory arrest of the heart comprising:

(a) an elongated catheter shaft configured to be advanceable from a peripheral vessel to and through at least two chambers of the heart, having a proximal end adapted to extend out of the patient and a distal end adapted to move through the chambers of the heart, said distal end having at least one fenestration;

(b) a succession of flow control members positioned along the catheter shaft such that after the catheter has been positioned in the patient's body, one or more of the flow control members are positioned within the patient's heart, and wherein the succession of flow control members comprises at least two flow control members which are positioned along the catheter shaft at desired locations to isolate subcirculation regions within the patient;

(c) means for perfusing the pulmonary arterial; and (d) means for draining at least one chamber of the heart.

23. A biventricular vascular catheter for providing access to a patient's heart for cardiopulmonary surgery, for cardiopulmonary circulatory support, and for circulatory arrest of the heart comprising:

(a) a first elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated, wherein such subcirculation region is selected from the group consisting of the coronary arterial, cerebral, pulmonary, neck and limb, spinal and thoracic subcirculations; and (b) a second elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated, wherein such subcirculation region is selected from the group consisting of the coronary arterial, cerebral, pulmonary, neck and limb, spinal and thoracic subcirculations.

24. The catheter system of claim 23, wherein the catheter system further comprises means for draining at least one chamber of the heart.

25. The catheter system of claim 23, wherein the succession of flow control members in one or more catheters includes one or more flow control members comprising an inflatable balloon.

26. The catheter system of claim 25, wherein the one or more inflatable balloons are independently inflatable.

27. The catheter system of claim 23, wherein the catheter system accommodates the selective perfusion or drainage of blood either seperately or at the same time.

28. A method for performing a surgical procedure using the catheter system of claim 23, the method comprising:

(a) advancing the first catheter of claim 23 to a location within a patient's heart from a peripheral vessel;

(b) advancing the second catheter of claim 23 to a location within a patient's heart from a peripheral vessel; and (c) selectively perfusing one or more subcirculation regions within the patient.

29. A biventricular vascular catheter for providing access to a patient's heart for cardiopulmonary surgery, for cardiopulmonary circulatory support, and for circulatory arrest of the heart comprising:

(a) a first elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated; and (b) a second elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated, wherein each succession of flow control members of each catheter comprises at least two flow control members which are positioned along the catheter shaft at desired locations to isolate circulation to the thorax and spinal column.

30. A biventricular vascular catheter for providing access to a patient's heart for cardiopulmonary surgery, for cardiopulmonary circulatory support, and for circulatory arrest of the heart comprising:

(a) a first elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated; and (b) a second elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation-region within the patient is isolated, wherein at least two flow control members which are positioned along the catheter shaft at desired locations to isolate drainage of the azygous veins.

31. A biventricular vascular catheter for providing access to a patient's heart for cardiopulmonary surgery, for cardiopulmonary circulatory support, and for circulatory arrest of the heart comprising:

(a) a first elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated:

(b) a second elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated; and (c) means for perfusing the pulmonary artery.

32. A biventricular vascular catheter for providing access to a patient's heart for cardiopulmonary surgery, for cardiopulmonary circulatory support, and for circulatory arrest of the heart comprising:

(a) a first elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated, (b) a second elongated catheter shaft configured to be advanceable from a peripheral vessel to and through at least two chambers of the heart, having a proximal end adapted to extend out of the patient and a distal end adapted to move through the chambers of the heart, said distal end having at least one fenestration, and a succession of flow control members positioned along the catheter shaft such that after the catheter has been positioned in the patient's body, one or more of the flow control members are positioned within the patient's heart and at least one subcirculation region within the patient is isolated;

(c) means for perfusing the pulmonary artery.

* * * * *